(12) United States Patent
Sadee et al.

(10) Patent No.: US 12,161,641 B2
(45) Date of Patent: *Dec. 10, 2024

(54) TREATMENTS AND PREVENTION OF OPIOID NEONATAL ABSTINENCE SYNDROME

(71) Applicant: Ohio State Innovation Foundation, Columbus, OH (US)

(72) Inventors: Wolfgang Sadee, Upper Arlington, OH (US); John Oberdick, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 45 days.

This patent is subject to a terminal disclaimer.

(21) Appl. No.: 17/180,945

(22) Filed: Feb. 22, 2021

(65) Prior Publication Data

US 2021/0205296 A1 Jul. 8, 2021

Related U.S. Application Data

(63) Continuation of application No. 16/068,593, filed as application No. PCT/US2017/012452 on Jan. 6, 2017, now Pat. No. 10,925,870.

(60) Provisional application No. 62/276,691, filed on Jan. 8, 2016.

(51) Int. Cl.
| | | |
|---|---|---|
| *A61K 31/485* | (2006.01) | |
| *A61K 31/4178* | (2006.01) | |
| *A61K 45/06* | (2006.01) | |
| *A61P 25/36* | (2006.01) | |

(52) U.S. Cl.
CPC ........ *A61K 31/485* (2013.01); *A61K 31/4178* (2013.01); *A61K 45/06* (2013.01); *A61P 25/36* (2018.01)

(58) Field of Classification Search
CPC .............................. A61K 31/485; A61P 25/36
See application file for complete search history.

(56) References Cited

U.S. PATENT DOCUMENTS

| | | | |
|---|---|---|---|
| 6,713,488 B2 | 3/2004 | Sadee et al. | |
| 8,748,448 B2 | 6/2014 | Sadee et al. | |
| 8,883,817 B2 | 11/2014 | Sadee et al. | |
| 9,061,024 B2 | 6/2015 | Sadee et al. | |
| 2003/0069262 A1* | 4/2003 | Sadee ............... | A61K 31/485 514/282 |
| 2006/0111308 A1 | 5/2006 | Robbins et al. | |
| 2006/0240085 A1 | 10/2006 | Reidenberg et al. | |
| 2010/0144754 A1* | 6/2010 | Peltz ............... | A61K 31/495 514/397 |
| 2011/0195433 A1 | 8/2011 | Sadee | |

FOREIGN PATENT DOCUMENTS

EP 2214672 10/2012

OTHER PUBLICATIONS

Hulse et. al. (J. Obstet. Gynecol. (2001) 41:424-428). (Year: 2001).*
Hulse et. al. (Aust. N. Z. J. Obstet. Gynaecol. (2002) 42:569-573). (Year: 2002).*
Hulse et. al. (Int. J. Gynaecol. Obstet. (2004) 85:170-171). (Year: 2004).*
Raehal et. al. (The Journal of Pharmacology and Experimental Therapies (2005) 313:1150-1162) . (Year: 2005).*
Yancey-Wrona (Life Sciences (2009) 413-420). (Year: 2009).*
Chey, William D., et al. "Naloxegol for opioid-induced constipation in patients with noncancer pain." New England Journal of Medicine 370.25 (2014): 2387-2396.
Clancy, B., R. B. Darlington, and B. L. Finlay. "Translating developmental time across mammalian species." Neuroscience 105.1 (2001): 7-17.
ClinicalTrials.gov, Jun. 26, 2014, NCT01965704. Can Ondansetron Prevent Neonatal Abstinence Syndrome (NAS) in Babies Born to Narcotic-dependent Women (AIM2NAS). 3 pages. https://clinicaltrials.gov/ct2/show/NCT01965704?term=NCT01965704&draw=2&rank=1.
Communication under Rule 71(3) EPC issued by the European Patent Office in European Application No. 17736392, dated Mar. 3, 2021. 40 pages.
Cortesi, R., C. Nastruzzi, and S. S. Davis. "Sugar cross-linked gelatin for controlled release: microspheres and disks." Biomaterials 19.18 (1998): 1641-1649.
Debelak, Kimber, et al. "Buprenorphine and naloxone in the treatment of opioid dependence during pregnancy—initial patient care and outcome data." The American journal on addictions 22.3 (2013): 252-254.
Dryden, C., et al. "Maternal methadone use in pregnancy: factors associated with the development of neonatal abstinence syndrome and implications for healthcare resources." BJOG: An International Journal of Obstetrics & Gynaecology 116.5 (2009): 665-671.
Elkomy, Mohammed H., et al. "Ondansetron pharmacokinetics in pregnant women and neonates: towards a new treatment for neonatal abstinence syndrome." Clinical Pharmacology & Therapeutics 97.2 (2015): 167-176.
Enters, E. Karl, et al. "The effect of prenatal methadone exposure on development and nociception during the early postnatal period of the rat." Neurotoxicology and teratology 13.2 (1991): 161-166.
Extended European Search Report issued by the European Patent Office in European Application No. 17736392, dated May 24, 2019, 5 pages.

(Continued)

Primary Examiner — Marcos L Sznaidman
(74) Attorney, Agent, or Firm — Meunier Carlin & Curfman LLC

(57) ABSTRACT

Disclosed is a method for reducing or preventing fetal opioid dependence in a drug dependent or opioid tolerant pregnant subject. The method involves administering to the pregnant subject a composition comprising an opioid antagonist in an amount effective to reduce or prevent fetal opioid dependence, wherein the opioid antagonist a) is orally available or delivered systemically and reaches the circulation of the pregnant subject, b) is substantially excluded from the subject's brain by the blood brain barrier, and c) penetrates the placenta and enters the fetal brain. The method also includes administering the opioid antagonist to the neonate in increasing amounts to facilitate weaning the neonate from continued opioid maintenance.

10 Claims, 4 Drawing Sheets

(56) References Cited

OTHER PUBLICATIONS

Farid et al. The Effects of Maternally Administered Methadone, Buprenorphine and Naltrexone on Offspring: Review of Human and Animal Data. Current Neuropharmacology, vol. 6, No. 2, (2008): 125-150.
Ginsberg, Gary, et al. "Evaluation of child/adult pharmacokinetic differences from a database derived from the therapeutic drug literature." *Toxicological Sciences* 66.2 (2002): 185-200.
Hall, Eric S., et al. "A multicenter cohort study of treatments and hospital outcomes in neonatal abstinence syndrome." *Pediatrics* (2014): peds—2013, e527-534.
Heslop, David. "On the statistical analysis of the rock magnetic S-ratio." *Geophysical Journal International* 178.1 (2009): 159-161.
Hommel, Gerhard. "A stagewise rejective multiple test procedure based on a modified Bonferroni test." *Biometrika* 75.2 (1988): 383-386.
Hothorn, Torsten, Frank Bretz, and Peter Westfall. "Simultaneous inference in general parametric models." *Biometrical journal* 50.3 (2008): 346-363.
Hulse, Gary K., G. O'neil, and D. E. Arnold-Reed. "Methadone maintenance vs. implantable naltrexone treatment in the pregnant heroin user." International Journal of Gynecology & Obstetrics 85.2 (2004): 170-171.
Hulse, G. K., et al. "Obstetric and neonatal outcomes associated with maternal naltrexone exposure." Australian and New Zealand Journal of Obstetrics and Gynaecology 41.4 (2001): 424-428.
Hulse, Gary, and G. O'neil. "Using naltrexone implants in the management of the pregnant heroin user." Australian and New Zealand Journal of Obstetrics and Gynaecology 42.5 (2002): 569-573.
International Search Report and Written Opinion. Application No. PCT/US2017/012452. Mailed Mar. 16, 2107. 9 pages.
Jaki, Thomas, Martin J. Wolfsegger, and Meinhard Ploner. "Confidence intervals for ratios of AUCs in the case of serial sampling: a comparison of seven methods." *Pharmaceutical Statistics: The Journal of Applied Statistics in the Pharmaceutical Industry* 8.1 (2009): 12-24.
Jaki, Thomas, and Martin J. Wolfsegger. "Estimation of pharmacokinetic parameters with the R package PK." *Pharmaceutical Statistics* 10.3 (2011): 284-288.
Jones, Kathy L., and Gordon A. Barr. "Ontogeny of morphine withdrawal in the rat." *Behavioral neuroscience* 109.6 (1995): 1189.
Jones, Hendrée E., et al. "Neonatal abstinence syndrome after methadone or buprenorphine exposure." *New England Journal of Medicine* 363.24 (2010): 2320-2331.
Kalvass, J. Cory, Tristan S. Maurer, and Gary M. Pollack. "Use of plasma and brain unbound fractions to assess the extent of brain distribution of thirty-four drugs: Comparison of unbound concentration ratios to in vivo P-glycoprotein efflux ratios." *Drug metabolism and disposition* (2007), 35, 660-666.
Kalvass, J. Cory, et al. "Pharmacokinetics and pharmacodynamics of seven opioids in P-glycoprotein-competent mice: assessment of unbound brain EC50, u and correlation of in vitro, preclinical, and clinical data." *Journal of Pharmacology and Experimental Therapeutics* 323.1 (2007): 346-355.
Kastin, Abba J., Mary A. Pearson, and William A. Banks. "EEG evidence that morphine and an enkephalin analog cross the blood-brain barrier." *Pharmacology Biochemistry and Behavior* 40.4 (1991): 771-774.
Kest, B., et al. "Naloxone-precipitated withdrawal jumping in 11 inbred mouse strains: evidence for common genetic mechanisms in acute and chronic morphine physical dependence." *Neuroscience* 115.2 (2002): 463-469.
Licensed pharmacist Certification Center of State Food and Drug Administration. Pharmaceutical professional knowledge (1) 7th Edition 2015. Feb. 28, 2015. 3 pages.

Liu, Xingrong, et al. "Use of cassette dosing approach to assess brain penetration in drug discovery." *Drug Metabolism and Disposition* (2012): dmd-111, 40, 963-969.
Lossinsky, Albert S., Andrzej W. Vorbrodt, and Henryk M. Wisniewski. "Characterization of endothelial cell transport in the developing mouse blood-brain barrier." *Developmental neuroscience* 8.2 (1986): 61-75.
Lötsch, Jörn, and Gerd Geisslinger. "Morphine-6-glucuronide." *Clinical pharmacokinetics* 40.7 (2001): 485-499.
Mainguet, P., and R. Fiasse. "Double-blind placebo-controlled study of loperamide (Imodium) in chronic diarrhoea caused by ileocolic disease or resection." *Gut* 18.7 (1977): 575-579.
Mangel, A. W., et al. "Clinical trial: asimadoline in the treatment of patients with irritable bowel syndrome." *Alimentary pharmacology & therapeutics* 28.2 (2008): 239-249.
Office Action issued by the Chinese National Intellectual Property Administration in CN Application No. 2017800152345 on Jan. 29, 2021. 16 pages, with English translation.
Office Action issued by the Japanese Patent Office in JP Application No. 2018-535324 on Nov. 10, 2020. 10 pages, with English translation.
Pacifici, Roberta, et al. "Effect of morphine and methadone acute treatment on immunological activity in mice: pharmacokinetic and pharmacodynamic correlates." *Journal of Pharmacology and Experimental Therapeutics* 269.3 (1994): 1112-1116.
Patrick, Stephen W., et al. "Neonatal abstinence syndrome and associated health care expenditures: United States, 2000-2009." *Jama* 307.18 (2012): 1934-1940.
Pettinati, Helen M., et al. "The status of naltrexone in the treatment of alcohol dependence: specific effects on heavy drinking." *Journal of clinical psychopharmacology* 26.6 (2006): 610-625.
Qian Zhiyu, China Medical Science and Technology Press, Pharmacology 4th Edition. p. 176, Aug. 31, 2015. 3 pages.
Raehal, Kirsten M., et al. "In vivo characterization of 6β-naltrexol, an opioid ligand with less inverse agonist activity compared with naltrexone and naloxone in opioid-dependent mice." *Journal of Pharmacology and Experimental Therapeutics* 313.3 (2005): 1150-1162.
Ribatti, Domenico, et al. "Development of the blood-brain barrier: A historical point of view." *The Anatomical Record Part B: The New Anatomist: An Official Publication of the American Association of Anatomists* 289.1 (2006): 3-8.
Richardson, Kimberlei A., et al. "Neonatal animal models of opiate withdrawal." *ILAR journal* 47.1 (2006): 39-48.
Ritz, Christian. "Toward a unified approach to dose-response modeling in ecotoxicology." *Environmental Toxicology and Chemistry* 29.1 (2010): 220-229.
Ritz, Christian, and Jens C. Streibig. "Bioassay analysis using R." *J Stat Softw* 12.5 (2005): 1-22.
Robinson, Susan E., and Melisa J. Wallace. "Effect of perinatal buprenorphine exposure on development in the rat." *Journal of Pharmacology and Experimental Therapeutics* 298.2 (2001): 797-804.
Russell, James, et al. "Antagonism of gut, but not central effects of morphine with quaternary narcotic antagonists." *European journal of pharmacology* 78.3 (1982): 255-261.
Sadée, Wolfgang, Danxin Wang, and Edward J. Bilsky. "Basal opioid receptor activity, neutral antagonists, and therapeutic opportunities." *Life sciences* 76.13 (2005): 1427-1437.
Schilling, Karl, John Oberdick, and René L. Schilling. "Toward an efficient and integrative analysis of limited-choice behavioral experiments." *Journal of Neuroscience* 32.37 (2012): 12651-12656.
Shannon, Harlan E., and Elizabeth A. Lutz. "Comparison of the peripheral and central effects of the opioid agonists loperamide and morphine in the formalin test in rats." *Neuropharmacology* 42.2 (2002): 253-261.
Sirohi, Sunil, et al. "The relative potency of inverse opioid agonists and a neutral opioid antagonist in precipitated withdrawal and antagonism of analgesia and toxicity." *Journal of Pharmacology and Experimental Therapeutics* 330.2 (2009): 513-519.
Van Dorp, Eveline LA, Aurora Morariu, and Albert Dahan. "Morphine-6-glucuronide: potency and safety compared with morphine." *Expert opinion on pharmacotherapy* 9.11 (2008): 1955-1961.

(56) References Cited

OTHER PUBLICATIONS

Wang, Zaijie, et al. "Accelerated communciation: Constitutive μ opioid receptor activation as a regulatory mechanism underlying narcotic tolerance and dependence." *Life sciences* 54.20 (1994): PL339-PL350.

Wang, Danxin, et al. "Inverse agonists and neutral antagonists at μ opioid receptor (MOR): possible role of basal receptor signaling in narcotic dependence." *Journal of neurochemistry* 77.6 (2001): 1590-1600.

Wang, Danxin, et al. "Basal signaling activity of μ opioid receptor in mouse brain: role in narcotic dependence." *Journal of Pharmacology and Experimental Therapeutics* 308.2 (2004): 512-520.

Wiegand, Samantha L., et al. "Buprenorphine and naloxone compared with methadone treatment in pregnancy." Obstetrics & Gynecology 125.2 (2015): 363-368.

Wolfsegger, Martin J., and Thomas Jaki. "Non-compartmental estimation of pharmacokinetic parameters in serial sampling designs." *Journal of pharmacokinetics and pharmacodynamics* 36.5 (2009): 479.

Workman, Alan D., et al. "Modeling transformations of neurodevelopmental sequences across mammalian species." *Journal of Neuroscience* 33.17 (2013): 7368-7383.

Xie, Rujia, et al. "The role of P-glycoprotein in blood-brain barrier transport of morphine: transcortical microdialysis studies in mdr1a (−/−) and mdr1a (+/+) mice." *British journal of pharmacology* 128.3 (1999): 563-568.

Yancey-Wrona, Janet E., et al. "6β-naltrexol preferentially antagonizes opioid effects on gastrointestinal transit compared to antinociception in mice." *Life sciences* 85.11-12 (2009): 413-420.

Yancey-Wrona, Janet, et al. "6β-naltrexol, a peripherally selective opioid antagonist that inhibits morphine-induced slowing of gastrointestinal transit: an exploratory study." *Pain Medicine* 12.12 (2011): 1727-1737.

Yuan, Chun-Su, and Joseph F. Foss. "Oral methylnaltrexone for opioid-induced constipation." *Jama* 284.11 (2000): 1383-1384.

Zagon, Ian S., and Patricia J. McLaughlin. "Increased brain size and cellular content in infant rats treated with an opiate antagonist." *Science* 221.4616 (1983): 1179-1180.

Japanese Patent Office. Decision of Rejection. JP Application No. 2018-535324. Issued Aug. 31, 2021. 5 pages.

Australian Intellectual Property Office. Examination Report No. 1. AU Application No. 2017206041. Issued Jul. 26, 2021. 5 pages.

NPS Medicinewise, "Buprenorphine with naloxone (Suboxone Sublingual Film) for opiate dependence", Sep. 1, 2011, <URL: https://www.nps.org.au/radar/articles/buprenorphine-with-naloxone-suboxone-sublingual-film-for-opiate-dependence> retrieved from internet on Jul. 21, 2021.

Chinese National Intellectual Property Office. Office Action. CN Application No. 201780015234.5. Issued Oct. 26, 2021. 8 pages.

Chinese National Intellectual Property Administration. Decision of Rejection issued in Chinese Application No. 2017800152345 on Apr. 2, 2022. 10 pages.

Canadian Intellectual Property Office. Office Action issued in Canadian Application No. 3010609 on Jan. 9, 2023. 5 pages.

Safa et al., Pharmacological Prevention of Neonatal Opioid Withdrawal in a Pregnant Guinea Pig Model, Frontiers in Pharmacy, Feb. 25, 2021, pp. 1-18.

Canadian Intellectual Property Office. Office Action issued in Canadian Application No. 3010609. Sep. 5, 2023. 4 pages.

Canadian Intellectual Property Office. Office Action issued in CA Application No. 3010609 on Jun. 13, 2024. 3 pages.

New Zealand Intellectual Property Office. Office Action issued in NZ Application No. 744112 on Jul. 9, 2024. 3 pages.

\* cited by examiner

TREATMENTS AND PREVENTION OF OPIOID NEONATAL ABSTINENCE SYNDROME

CROSS-REFERENCE TO RELATED APPLICATIONS

This application is a continuation application of U.S. application Ser. No. 16/068,593 filed Jul. 6, 2018, which is a national stage application filed under 35 U.S.C. § 371 of PCT/US2017/012452 filed Jan. 6, 2017, which claims benefit of U.S. Provisional Application No. 62/276,691, filed Jan. 8, 2016, each of which are expressly incorporated herein by reference.

STATEMENT REGARDING FEDERALLY SPONSORED RESEARCH

This invention was made with government support under TR001070 and HD092011 awarded by the National Institutes of Health. The government has certain rights in the invention.

FIELD

The present invention relates to compounds, compositions, and methods for the treatment and prevention of opioid neonatal abstinence syndrome.

BACKGROUND

Illicit drug use by pregnant women is a growing national concern, with an estimated prevalence of ~16% in pregnant teens and ~7% in women 18-25 years old (Patrick S W, et al. (2012) JAMA 307:1934-1940). The frequency of infants with opiate dependence at birth, evidenced as neonatal abstinence syndrome (NAS), has been estimated at 3.39 per 1000 births as of 2009 (Patrick S W, et al (2012) JAMA 307:1934-1940). A large proportion of such births are from mothers engaged in managed methadone or buprenorphine treatment under a physician's care (Patrick S W, et al. (2012) JAMA 307:1934-1940, Jones H E, et al. (2010) N Engl J Med. 363:2320-2331), providing a target group for introduction of a prenatal therapy could one be devised. NAS infants are often born prematurely and display a range of symptoms, underweight, breathing and feeding difficulties, irritability, feeding intolerance, emesis, and seizures (Dryden, C, et al. (2009) BJOG 116:665-671; Patrick S W, et al. (2012) JAMA 307:1934-1940). NAS presents a huge financial burden for society because of long intensive care retention times and likely effects on long-term cognitive, emotional and social development of affected children. The consensus strategy for newborns with NAS is oral methadone. While stringent protocol-based treatment is a key factor in reducing length of hospital stay (Hall E S, et al. (2014) Pediatrics 134:e527-534), national standards governing the therapeutic weaning strategy are lacking. A common goal of current strategies is to alleviate withdrawal only after the newborn has already become dependent, whereas antepartum strategies preventing development of neonatal dependence in the first place are lacking.

SUMMARY

Disclosed herein are methods to reduce or prevent opioid neonatal abstinence syndrome (NAS). In one aspect, disclosed is a method for reducing or preventing opioid dependence in a fetus carried by a drug dependent or opioid tolerant pregnant subject receiving opioid therapy or maintenance (to reduce or prevent neonatal abstinence syndrome (NAS)). The method involves administering to the pregnant subject a composition comprising an opioid antagonist in an amount effective to reduce or prevent fetal opioid dependence, wherein the opioid antagonist a) is orally available and reaches the circulation of the pregnant subject, b) is substantially excluded from the pregnant subject's brain by the blood brain barrier, and c) penetrates the placenta and enters the fetal brain.

In some embodiments, the opioid antagonist is administered systemically (for example, subcutaneously in a sustained release formulation, or transdermally) while being substantially excluded from the subject's brain by the blood brain barrier, and penetrating the placenta and entering the fetal brain.

In some embodiments, the opioid antagonist is a neutral antagonist and not an inverse agonist. In particular embodiments, the opioid antagonist comprises 6β-naltrexol. In some embodiments, the opioid antagonist does not comprises naloxone or naltrexone.

In some embodiments, the composition comprises a sustained drug release formulation. In some cases, the method further comprises administering to the subject a palliative therapy.

In an additional embodiment, the opioid antagonist therapy is continued after birth of the newborn (neonate or infant) in increasing amounts effective to facilitate weaning the neonate from continued opioid maintenance administered when neonatal abstinence is observed.

Further disclosed herein is a method for treating neonatal withdrawal or abstinence syndrome, comprising:

prenatally administering to a drug dependent or opioid tolerant pregnant subject a first composition comprising an opioid antagonist in an amount effective to treat the neonatal withdrawal or abstinence syndrome, wherein the opioid antagonist reaches the circulation of the pregnant subject but is substantially excluded from the pregnant subject's brain by the blood brain barrier, and wherein the opioid antagonist penetrates the placenta and enters the fetal brain; and postnatally administering to a drug dependent or opioid tolerant infant subject a second composition comprising the opioid antagonist in increasing amounts effective to facilitate weaning the infant from continued opioid maintenance administered when neonatal abstinence is observed.

The details of one or more embodiments of the invention are set forth in the accompa-nying drawings and the description below. Other features, objects, and advantages of the invention will be apparent from the description and drawings, and from the claims.

BRIEF DESCRIPTION OF DRAWINGS

FIG. 1A shows 6β-naltrexol levels in embryonic and adult brain at four different survival times after a single drug injection. FIG. 1B shows 6β-naltrexol levels in embryonic and adult liver at four different survival times after drug injection. In FIGS. 1A & 1B the curve for adult plasma is superimposed for comparison to solid tissues Asterisks in A indicate significant differences between adult and embryonic brain at individual survival times. $*p<0.05$; $**p<0.01$. Number of samples (n) is indicated in Table 1.

FIG. 2A shows levels of drug in plasma, brain and liver after a single injection at PD7, PD14, PD20, PD32, and PD50. Embryonic (ED17) and adult (>2 mo. old) data from FIG. 1 were added for comparison purposes. 45 min survival time for all data. For the PD7 liver sample note that the data bar was truncated to better illustrate the broad range of drug levels across all tissues. Drug levels in most tissues at E17, PD7 and PD14 are significantly higher than in the corresponding tissues at PD20, PD35 and PD50 ($p<0.05$ by t-test; not indicated in figure). Similarly, drug levels in all adult tissues are significantly higher than corresponding tissues at PD32 ($p<0.05$ by t-test; not indicated in figure). FIG. 2B shows a comparison of drug levels in plasma, brain and liver at PD20 and PD32 with two survival times, 20 and 45 mins. Data for embryonic and adult tissues from FIG. 1 have been added for comparison. Asterisks in FIGS. 2A and 2B indicate plasma vs brain differences at a particular age; *$p<0.05$; **$p<0.01$. N=2 for all samples at PD7-PD50 (except plasma at PD7; n=1); for ED17 and adults n is indicated in FIG. 1 and Table 1.

FIG. 3A shows 6β-naltrexol prevents a dependence behavior, ithdwrawal jumping, when delivered in combination with morphine. Total jumps were counted over a period of 15 minutes starting immediately after the injection of naloxone to induce withdrawal. Two concentration ramping procedure were used for the morphine injections with commensurate ramping of 6β-naltrexol. Data are plotted using the lower of the two drug concentrations. Asterisks indicate a significant difference compared to morphine treated animals with no 6β-naltrexol; *$p<0.05$; **$p<0.01$. FIG. 3B shows jumps from FIG. 3A separated into ten 1.5 min. time bins. Bidirectional arrows indicate the time bin for each 6β-naltrexol dose where an equal number of jumps occur prior to and after that time bin. Note that this timepoint increases with increasing 6β-naltrexol. Asterisk indicates a significant effect of the 1/3000, 1/1000, and 1/200 doses of 6β-naltrexol compared to morphine-alone in the first three time bins. FIG. 3C shows inhibition of weight gain by morphine is alleviated by 6β-naltrexol. The mass of each mouse was determined before and after the 6 day morphine dosing schedule and the percent weight change was determined. Asterisk indicates significant difference from animals that received morphine but no ("0") 6β-naltrexol ($p<0.05$). In FIG. 3A, the number in parentheses indicates the number of animals tested at each drug concentration. In FIGS. 3B and 3C, drug concentration is reported as a ratio of 6β-naltrexol to morphine in order to emphasize the combination treatment.

DETAILED DESCRIPTION

Figure 1A:
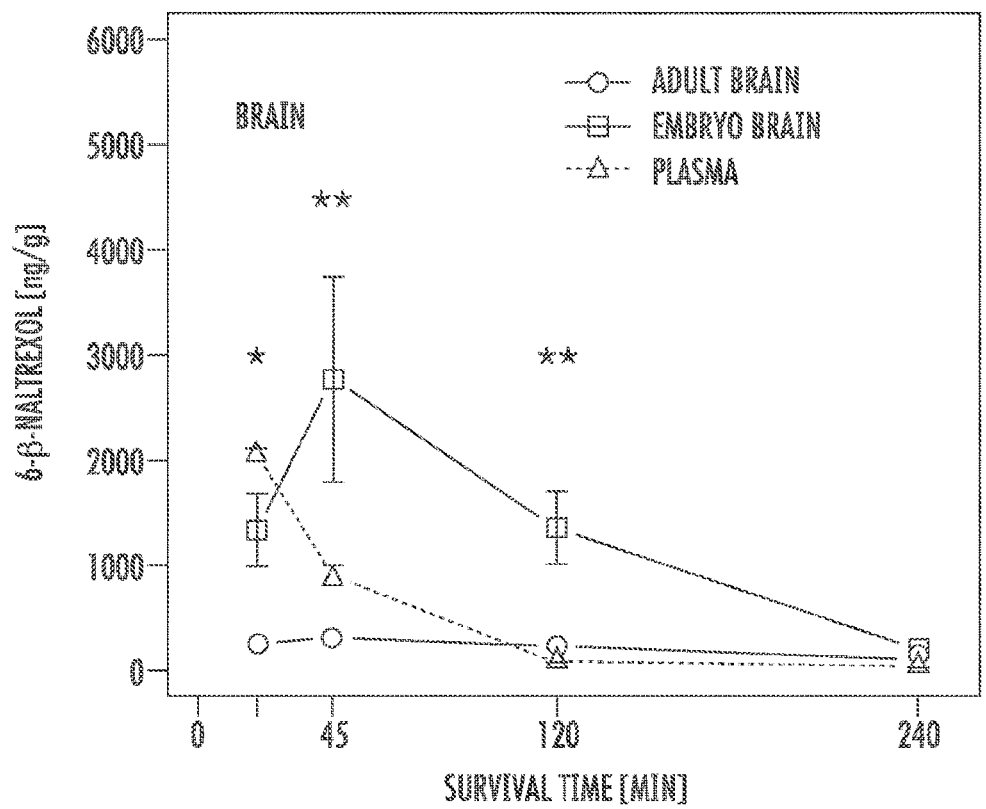
FIGS. 1A and 1B are graphs showing 6β-naltrexol levels in mice in embryonic (-□-) and adult (-•-) brain (FIG. 1A) and liver (FIG. 1B) as a function of survival time (min).

Disclosed herein are methods to reduce or prevent opioid neonatal abstinence syndrome (NAS). In one aspect, disclosed is a method for reducing or preventing opioid dependence in a fetus carried by a drug dependent or opioid tolerant pregnant subject receiving opioid therapy or maintenance (to reduce or prevent neonatal abstinence syndrome (NAS)). The method involves administering to the pregnant subject a composition comprising an opioid antagonist in an amount effective to reduce or prevent fetal opioid dependence, wherein the opioid antagonist a) is orally available and reaches the circulation of the pregnant subject, b) is substantially excluded from the pregnant subject's brain by the blood brain barrier, and c) penetrates the placenta and enters the fetal brain.

In some embodiments, the opioid antagonist is administered systemically (for example, subcutaneously in a sustained release formulation, or transdermally) while being substantially excluded from the subject's brain by the blood brain barrier, and penetrating the placenta and entering the fetal brain.

In an additional embodiment, the opioid antagonist therapy is continued after birth of the newborn in increasing amounts effective to facilitate weaning the neonate from continued opioid maintenance administered when neonatal abstinence is observed.

Further disclosed herein is a method for preventing neonatal withdrawal or abstinence syndrome, comprising:

prenatally administering to a drug dependent or opioid tolerant pregnant subject a first composition comprising an opioid antagonist in an amount effective to reduce or prevent opioid dependence in the fetus, wherein the opioid antagonist reaches the circulation of the pregnant subject but is substantially excluded from the pregnant subject's brain by the blood brain barrier, and wherein the opioid antagonist penetrates the placenta and enters the fetal brain; and postnatally administering to a drug dependent or opioid tolerant infant subject a second composition comprising the opioid antagonist in increasing amounts effective to facilitate weaning the infant from continued opioid maintenance administered when neonatal abstinence is observed.

Also disclosed herein is a method for treating withdrawal or abstinence syndrome in a drug dependent or opioid tolerant pregnant subject, comprising administering to the subject a composition comprising an opioid antagonist in an amount effective to treat the withdrawal or abstinence syndrome, wherein the opioid antagonist reaches the circulation of the pregnant subject but is substantially excluded from the subject's brain by the blood brain barrier, and wherein the opioid antagonist penetrates the placenta and enters the fetal brain.

In some embodiments, the amount of opioid antagonist postnatally administered to the infant is higher on a per weight basis than the dose administered prenatally to the pregnant subject. For example, the infant's blood brain barrier has continued to mature and thus a higher dose may be needed to reach the newborn's brain.

In some embodiments, the opioid antagonist is a neutral antagonist and not an inverse agonist. For example, in preferred embodiments, the opioid antagonist does not comprises naloxone or naltrexone. In particular embodiments, the opioid antagonist comprises 6β-naltrexol.

In some embodiments, the composition comprises a sustained drug release formulation. In some cases, the method further comprises administering to the subject a palliative therapy. In some cases, the method further comprises administering to the subject a 5-HT antagonist. In one embodiment, the 5-HT antagonist is ondansetron.

In some embodiments, the opioid antagonist is delivered in two daily subdoses. In some embodiments, the opioid antagonist is delivered in a daily dosage range from about 0.1 mg to about 100 mg. In some embodiments, the opioid antagonist is orally available.

The term "subject" or "host" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder, preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The compositions disclosed can be used therapeutically in combination with a pharmaceutically acceptable carrier. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The compounds described herein, or their salt, isotopic analog, or prodrug can be administered to the host using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases. Pharmaceutical formulations can be prepared for any desired route of administration including, but not limited to, systemic, topical, oral, intravenous, subcutaneous, transdermal, percutaneous (with optional penetration enhancers), buccal, sublingual, rectal, intraaortal, intranasal, parenteral, or aerosol administration. Some of these administration routes may avoid the first-pass effects in the liver. Formulations for parenteral administration include, but are not limited to, suspensions, solutions, emulsions in oily or aqueous vehicles, pastes, and implantable sustained-release or biodegradable formulations.

For oral administration a pharmaceutical composition can take the form of solutions, suspensions, tablets, pills, capsules, powders, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In one embodiment, the disclosed opioid antagonist is administered to a subject (for example, a human subject) in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of opioid antagonist administered to achieve a therapeutic effective dose is about 0.1 ng, 1 ng, 10 ng, 10 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater. In one embodiment, the dosage range is from about 0.1 mg to about 100 mg when given orally. In one embodiment, the dosage range is from about 0.001 mg to about 1 mg per kg of body weight when given orally.

In one embodiment, the daily dosage can be administered in two (or more) daily subdoses.

In one embodiment, the disclosed opioid antagonist is administered in a controlled-release implant or depot. In one embodiment, if a slow release formulation is implanted, it may bypass the GI tract and liver, and thus a fifth of the dosage is needed per day (for example, if the bioavailability is about 20%). Pharmaceutical formulations can be designed for immediate release, sustained release, or delayed release of one or more opioid antagonists in a therapeutically effective amount. In one embodiment, the formulation provides a sustained release. The compounds described herein can be formulated for parenteral administration. Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads.

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

The term "carrier" includes but is not limited to diluents, binders, lubricants, disintegrators, fillers, matrix-forming compositions and coating compositions. "Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6$^{th}$ Edition, Ansel et. al., (Media, PA: Williams and Wilkins, 1995) which provides information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate, dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamert 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

The delayed-release portion is designed to enable drug release after a defined period of time. In one embodiment, in the case of an orally delivered formulation, this would be in the upper part of the gastrointestinal (GI) tract. Delayed release in an oral formulation can be achieved using enteric coatings. The enteric coated formulation remains intact or substantially intact in the stomach but dissolves and releases the contents of the dosage form once it reaches the small intestine or large intestines. Other types of coatings can be used to provide delayed release following injection subcutaneously, intra-tissue or intramuscularly at a site near or at the area to be treated.

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

Opioid antagonists can be administered adjunctively with other active compounds such as analgesics, anti-inflammatory drugs, antipyretics, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, parasympathomimetics, stimulants, anorectics and anti-narcoleptics.

In some embodiments, the opioid antagonists can be administered in combination with other active compounds including a 5HT antagonist. In one embodiment, the 5-HT antagonist is ondansetron. Additional examples of 5-HT (or 5-HT$_3$) antagonists include, ergot alkaloids, granisetron, metoclopramide, trimethobenzamide, tropisetron, dolasetron, batanopride, zacopride, azasetron, ramosetron, lerisetron, cilansetron, itasetron, and indisetron.

A number of embodiments of the invention have been described. Nevertheless, it will be understood that various modifications may be made without departing from the spirit and scope of the invention. Accordingly, other embodiments are within the scope of the following claims.

EXAMPLES

Example 1. Delivery of an Opioid Antagonist to the Fetal Brain in Pregnant Mice

Methods
Animals

Mice of the C57BL/6NTac strain were produced in a breeding colony at Ohio State. Animals were housed in micro-isolator racks with positive air-flow and 24 hr access to food and water. They were kept on a 12:12 light dark cycle. All procedures were approved by The Ohio State University Institutional Animal Care and Use Committee and are in compliance with guidelines established by the National Institutes of Health published in Guide for the Care and Use of Laboratory Animals.

Drug Dosing and Tissue Collection

6β-naltrexol and naltrexone were provided by the National Institute for Drug Addiction (NIDA) as previously reported (Wang, D, et al. (2004) J Pharmacol Exp Ther 308:512-520). Drugs were dissolved in saline at concentrations between 10 and 20 mg/ml, and all dilutions were made in saline. Morphine was purchased from the Ohio State Medical Center pharmacy as a 15 mg/ml solution in saline. Animals were injected subcutaneously in the region around the right hind-quarters. Injection volume typically did not exceed 150 µl (juveniles ranged from 50-100 µl), and the drug dose in most cases was 10 mg/kg (except for the behavior studies as indicated below). After injection and variable survival times adult and pregnant mice were euthanized by cervical dislocation, and brain, liver and plasma were collected, quickly frozen on dry-ice and stored at −70° C. until processing After euthanizing the dam, embryos were collected into a large (150×15 mm) petri dish and kept on ice while maternal tissues were processed. All embryonic tissues were then dissected and collected in a cold room at 4° C. in order to facilitate and preserve tissue integrity during dissection, then stored at −70° C. Tissues from pregnant mice and embryos that had been dosed with 6β-naltrexol or naltrexone (pregnant female was dosed subcutaneously with 10 mg/kg) were resected, weighed, and quickly frozen on dry ice in individual microcentrifuge tubes. Samples were later thawed, processed and analyzed via liquid chromatography-tandem mass spectrometry (LC-MS/MS) to quantify levels of drug. Detailed methods for tissue processing and LC-MS/MS analysis are located in the supplemental information.

Analysis of Dependence Behaviors in Early Postnatal Mice

Animals were injected with morphine alone or morphine mixed with increasing amounts of 6β-naltrexol. Injections were started on postnatal day 12 (PD12) and continued for 5 days. On days 1-3 morphine was injected at 10 mg/kg, and at 20 mg/kg on days 4 and 5. On day 6 (PD18) a final injection of 20 mg/kg was made, and 3 hours later mice were injected with 30 mg/kg naloxone to induce withdrawal. All injections were subcutaneous. When Morphine was co-injected with 6β-naltrexol the latter was held at a constant ratio when the Morphine dose was increased on days 4-6. Because of the changing Morphine dosages the 6β-naltrexol dose is reported as a ratio relative to Morphine, or as a dose range. Immediately upon injection with naloxone mice were placed in a clear plastic container with a 6 inch square base and 10 inches tall, with a lid. Withdrawal jumping was videotaped and jumps were scored in a 15 minute interval.

Statistical Analysis

Summary data are presented as means+1 SEM unless otherwise indicated Continuous data (drug concentrations) were analyzed using one-way ANOVA and post hoc comparisons were made using either Dunnett's procedure (for one-to-many comparisons) or t-tests (for all-pairs contrasts). In the latter case, p-values were adjusted for multiple comparisons using Hommel's method (Hommel, G. (1988) Biometrika 75:383-386). Data were log transformed to account for heteroscedasticity. When ratio values such as the brain/plasma ratio were compared, these were log-transformed before analysis to account for the constrained structure of ratio variables (e.g., Heslop, D. (2009) Geophys. J. Int. 178:159-161; Schilling K, et al. (2012) J Neurosci. 32:12651-12656). The dependence of jumping behavior on 6β-naltrexol levels was modelled using a 4-parametric log-normal curve taking into account that the response was a count variable. AUCs were integrated over the time span analyzed (i.e., from 0 to 240 min; Wolfsegger, M J, et al. (2009) J Pharmacokinet Pharmacodyn 36:479-494). Confidence intervals for AUCs were obtained by bootstrapping, as recommended in Jaki & Wolfsegger (Jaki, T, et al (2009) Pharmaceutical Statistics 8:12-24). All statistical procedures were implemented in R (R Core Team, 2015), using the packages multcomp (Hothorn, T, et al. (2008) Biometrical Journal 50:346-363) for multiple comparisons, PK (Jaki, T, et al. (2011) Pharmaceutical Statistics 10:284-288) for pharmacokinetic analyses, and drc (Ritz, C, et al. (2005) Bioassay analysis using R. J. Stat. Softw. 12:22) for dose-response fitting.

Liquid Chromatography/Mass Spectrometry Analysis for Drug Quantification in Tissue Samples Blank mouse plasma, brain and liver tissues were obtained, weighed, and quickly frozen on dry ice in individual microcentrifuge tubes. The brain and liver samples were made into separate tissue homogenates with Omni-Inc GLH-01 homogenator with a final concentration of 0.5 mg/ml tissue in 50% methanol. Each tissue was aliquoted into 100 µl 1.5 ml microcentrifuge tubes for future use in standard curves or for use as QC's.

Tissues from pregnant mice and embryos that had been dosed with 6β-naltrexol or naltrexone (pregnant female was dosed subcutaneously with 10.0 mg/kg) were resected, weighed, and quickly frozen on dry ice in individual microcentrifuge tubes. They were then thawed on ice and homogenized with Omni-Inc GLH-01 homogenator with a final concentration of 0.5 mg/mi tissue in 50% methanol. Mouse embryo brains and mouse embryo livers each were pooled to obtain adequate quantities for analysis. Each sample was aliquoted into 100 µl 1.5 ml microcentrifuge tubes. Each standard concentration sample was then spiked with 10 µl internal standard (IS) nalbuphine at 2000 ng/ml to obtain a final concentration of 200 ng/ml. The samples for each curve were then extracted with the addition of 1 ml of 4° C. 100% methanol, vortex mixed vigorously for 30 seconds then centrifuged at 13,000 g's for 10 minutes. The liquid from each tube was then decanted to new 5 ml glass test tube. Each tube was then placed in a nitrogen evaporator system until completely dry (~2.5 hours). 120 μl of 10 mM ammonia formate and 0.1% formic acid was used to resolubilize the contents of each tube. The tubes were vortex mixed and centrifuged at 13,000 g for 10 minutes. 80 μl supernatant was then placed into a liquid chromatography autosampler compatible tubes along with standard curve and quality control samples for analysis on a Thermo Accela UHPLC and Thermo Discovery TSQ Triple Quadrapole Mass Spectrometer.

Calibration standards were prepared as follows. A dilution series of combined naltrexol, naltrexone, and naltrexamide in 50% methanol was made at the following concentrations: 5000, 2000, 1000, 500, 200, 100, 50, 20, 10, and 5 ng/mL. 10 μl of each of these standards was added to 100 μl of thawed plasma and tissue homogenates to make final concentrations of 500, 200, 100, 50, 20, 10, 5, 2, 1, and 0.5 ng/mL Each standard concentration sample was then spiked with 10 μl the internal standard (IS) nalbuphine at 2000 ng/ml to obtained a final concentration of 200 ng/ml. The samples for each curve were then extracted with the addition of 1 ml of 4° C. 100% methanol. They were then vortex mixed vigorously for 30 seconds and centrifuged at 13,000×g for 10 minutes. Supernatant from each tube was transferred to new 5 ml glass test tubes and dried in a nitrogen evaporator system (~2.5 hours). 120 μl of 10 mM ammonia formate and 0.1% formic acid was used to resolubilize the contents of each tube. The tubes were vortex mixed, aliquoted into new microcentrifuge tubes and centrifuged at 13,000 g for 10 minutes. 80 μl liquid was transferred into autosampler compatible tubes for analysis. 20 μl of each sample were injected into LC-MS system.

For chromatographic separation a Thermo Accela UHPLC with an Agilent Zorbax 5 μm SB-Phenyl 2.1×50 mm column and a gradient of 0.1% formic acid, 10 mM ammonia formate in water and 0.1% formic acid, 10 mM ammonia formate in methanol was used to separate components of each injected sample (20 μl). The gradient consisted of 20% methanol for the first 1.0 minute with transitions to 50% and 90% methanol to 2.0 and 2.5 minutes, respectively. At 4.0 minutes the composition was immediately switched from 90% to 20% methanol, and the column was equilibrated until the end of the run at 5.5 minutes. Flow was maintained at 400 ul/min.

The samples were analyzed on a Thermo TSQ Quantum Discovery Max with an electrospray ionization (ESI) source in positive mode. Mass transitions (m/z) using single reaction monitoring were 344.23>254.17 and 344.23>326.23 for naltrexol, 342.18>270.15 and 342.18>324.21 for naltrexone, 385.25>211.12 and 385.25>367.25 for naltrexamide, and 358.1>340.16 for the internal standard nalbuphine.

Results

6β-Naltrexol and Naltrexone Levels in Embryonic and Adult Tissues

Figure 1B:
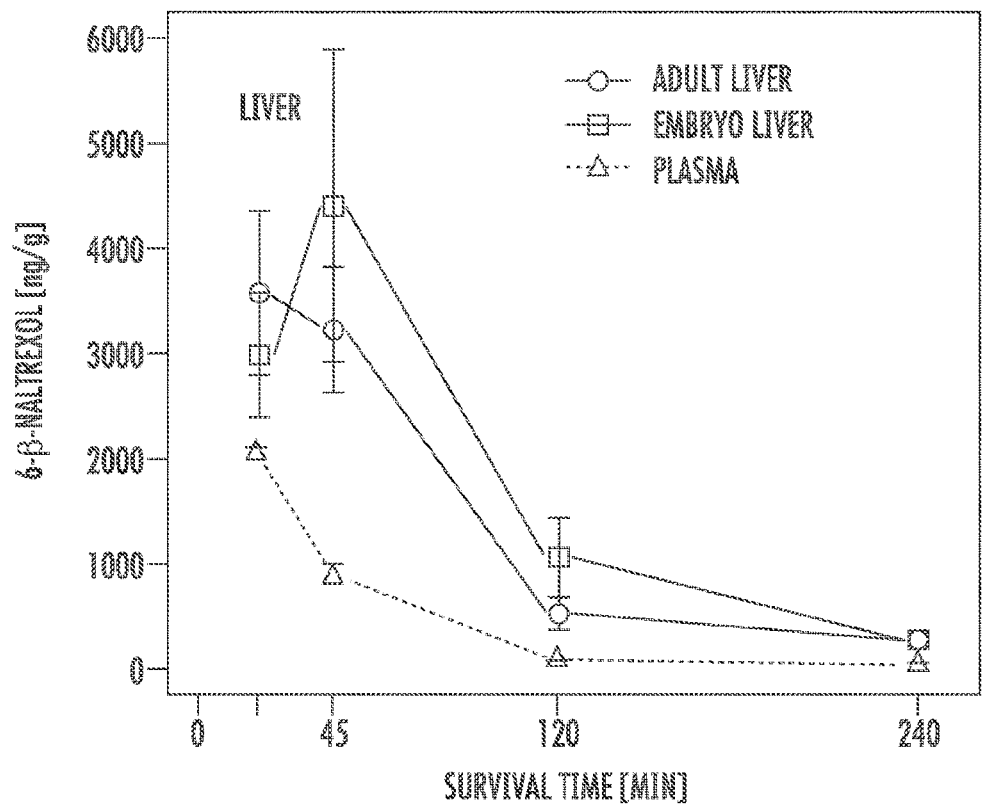

Previous studies using mass spectrometry showed that brain levels of 6β-naltrexol are ~10-fold lower than plasma levels in adult mice 10 minutes after injection, whereas the levels of naltrexone, an FDA approved opioid antagonist used to treat alcoholism, are roughly equivalent in plasma and brain (see Table 1 in Wang, D, et al. (2004) J Pharmacol Exp Ther 308:512-520). This result indicates that 6β-naltrexol has limited access to the adult brain compared to naltrexone, which is due to the blood brain barrier (BBB). However, if 6β-naltrexol is able to pass through the placenta, it may be able to enter the fetal brain because of an undeveloped BBB. To test this, pregnant and non-pregnant adult female mice were injected with 6β-naltrexol or naltrexone, and the drug levels were measured in maternal and adult plasma, brain and liver, and in embryonic brain and liver, using mass spectrometry. Four different survival times were examined post-injection. As shown in FIG. 1 and Table 1, 6β-naltrexol levels in mice are significantly higher in embryonic brain than adult brain at 20, 45, and 120 minutes postinjection, and drop to low residual levels at both ages after 4 hrs. At peak, embryonic brain levels are ~9-fold higher than in adult brain. In contrast, levels in embryonic and adult liver are roughly comparable to one another, indicating that 6β-naltrexol enters the fetal circulation rapidly. Moreover, 6β-naltrexol levels in adult and embryonic liver are not significantly different from embryonic brain levels (p>0.05), supporting the finding that 6β-naltrexol diffuses unimpeded into fetal brain.

TABLE 1

Time-course of 6β-naltrexol levels in mice in adult and embryonic brain and liver

|  | 20 min | 45 min | 2 hrs | 4 hrs |
| --- | --- | --- | --- | --- |
| Plasma | 2060 ± 110 (n = 3) | 930 ± 220 (n = 5) | 90 ± 50 (n = 4) | 40 ± 40 (n = 4) |
| Adult Brain | 260 ± 70 (n = 3) | 310 ± 70 (n = 7) | 230 ± 30 (n = 4) | 110 ± 40 (n = 4) |
| Embryo Brain | 1350 ± 490 (n = 2) | 2780 ± 1670 (n = 3) | 1370 ± 500 (n = 2) | 210 ± 60 (n = 2) |
| Adult Liver | 3570 ± 1360 (n = 3) | 3200 ± 1600 (n = 7) | 530 ± 320 (n = 4) | 280 ± 160 (n = 4) |
| Embryo Liver | 2970 ± 830 (n = 2) | 4400 ± 2580 (n = 3) | 1040 ± 540 (n = 2) | 250 ± 50 (n = 2) |

Naltrexol levels in ng/g tissue at different survival times;
dosage = 10 mg/kg delivered subcutaneously The measured 6β-naltrexol levels were also examined using a non-compartmental pharmacokinetic model. The area under the curve (AUC) for embryonic brain was 6-fold greater than that of adult brain (302+60×10³ ng/ml-min with 95% CI of 146-1060 for embryonic brain vs 49+2×10³ with 95% CI of 44-54 for adult brain; significant based on 95% confidence intervals). In contrast the AUC for adult vs embryonic liver was not significantly different (274+36×10³ ng/ml-min with 95% CI of 208-372 for adult liver and 373+84 with 95% CI of 46-1380 for embryonic liver).

The ratios between tissues and plasma (KP ratios, brain:plasma or liver:plasma) were also examined to get a measure of tissue exclusion or retention (Liu, X, et al. (2012) Drug Metab. Dispos. 40:963-969; Kalvass, J. C, et al. (2007a) Drug Metab. Dispos. 35:660-666). Consistent with previous results (Wang et al., 2004), the adult brain KP ratio for 6β-naltrexol was 0.13 at 20 min survival (p<0.0001 for difference from unity) and 0.34 at 45 minutes (p<0.0001 for difference from unity; see also Table 1), showing a barrier to drug entry into the brain. The brain KP ratio based on AUC's was 0.58 and was significantly different from unity based on 95% CI's, again supporting adult brain exclusion of drug (83+6×10³ ng/ml-min with 95% CI of 70-98×10³ for plasma and 49+2×10³ with 95% CI of 44-54×10³ for adult brain). The greater KP ratio calculated based on AUC's integrated over 4 hrs compared to single time-points reflects the more rapid elimination of 6β-naltrexol from the circulation than from the brain in mice (see FIG. 1); therefore, KP ratios measured under non-equilibrium conditions can vary with time as a function of rate of elimination and tissue distribution.

In contrast, the fetal brain:maternal plasma KP ratio was 2.7 at 45 min. after drug injection ($p<0.05$ for difference from unity; see FIGS. 1 & 2) and the ratio was 15.7 at 120 min after injection ($p<0.01$ for difference from unity) (see FIGS. 1 & 2). At an earlier time point (20 min after injection) the fetal brain KP ratio is not significantly different from unity ($p>0.05$), indicating rapid entry into fetal brain, and longer persistence than in maternal blood (FIG. 1). The fetal brain KP ratio based on non-compartmental AUC's is 3.6, which is significantly different from unity (83+6×10³ ng/ml-min with 95% CI of 70-98×10³ for maternal plasma and 302+60×10³ with 95% CI of 146-1060×10³ for fetal brain). Similarly the KP ratios based on AUC's is 4.3 for fetal liver and 2.6 for adult liver. Thus, in contrast to relative exclusion of 6β-naltrexol from the adult brain, drug levels in fetal brain, and fetal and adult liver, are consistently higher than those in plasma. Owing to rapid elimination, 6β-naltrexol is largely depleted from all tissues between 2 and 4 hours after injection (FIG. 1 and Table 1).

In contrast to the relative exclusion of 6β-naltrexol from the adult brain, naltrexone (the parent compound) has free access to the brain (Table 4) confirming previous results (see Kastin, A J, et al. (1991) Pharmacol Biochem Behav 40:771-774; Wang, D, et al. (2004) J Pharmacol Exp Ther 308:512-520). The contrast of low 6β-naltrexol and high naltrexone levels in adult brain highlights the relative exclusion of 6β-naltrexol by the intact BBB.

son of fetal vs adult brain after 4 injections). These results indicate that while 6β-naltrexol gains some limited access to adult brain, it is not substantially retained upon multiple injections, a finding relevant to a potential therapy dosage regimen.

TABLE 2

Comparison of survival vs cumulative injections of 6β-naltrexol at 4 hr survival time-point.

|  | 1 injection | 4 injections in 24 hrs |
|---|---|---|
| Plasma | 40 ± 40 (n = 4) | 60 ± 20 (n = 2) |
| Adult Brain | 110 ± 40 (n = 4) | 160 ± 20 (n = 2) |
| Embryo Brain | 210 ± 60 (n = 2) | 290 ± 40 (n = 2) |
| Adult Liver | 280 ± 160 (n = 4) | 360 ± 50 (n = 2) |
| Embryo Liver | 250 ± 50 (n = 2) | 500 ± 190 (n = 2) |

1 versus 4 injections of 10 mg/kg 6β-naltrexol with 4 hr survival time

Analysis of 6β-Naltrexol Levels in Brain During Postnatal Development

Previous studies have been mixed in demonstrating robust withdrawal behaviors at birth in rodents, ranging from weak effects in rats (Enters E K, et al. (1991) Neurotoxicol Teratol. 13:161-166, Robinson S E, et al. (2001) J Pharmacol Exp Ther. 298:797-804), to no effects in mice (Richardson K A, et al. (2006) ILAR J. 47:39-48). Using the same opiate delivery paradigm in pregnant rats more robust withdrawal behaviors are detectable 7 days after birth, and similarly, if morphine is delivered by direct injection in rat pups anytime after postnatal day 7 (PD7), robust pre-weaning withdrawal behaviors can be induced by naloxone (Jones, K L, et al. (1995) Behav. Neurosci. 109:1189-1198). The refractoriness of the newborn rodent to easily observable dependence behaviors is likely due, at least in part, to the developmental state of the brain: mouse and rat brains at birth are devel-

TABLE 4

Time-course of Naltrexone levels in adult and embryonic brain and liver

|  | 20 min | 45 min | 2 hrs | 4 hrs |
|---|---|---|---|---|
| Plasma | 1880 (n = 1) | 620 ± 380 (n = 3) | 130 ± 90 (n = 3) | 4 (n = 1) |
| Adult Brain | 3230 (n = 1) | 1470 ± 640 (n = 3) | 250 ± 120 (n = 3) | 18 (n = 1) |
| Embryo Brain | ND | 2610 (n = 1) | 500 (n = 1) | ND |
| Adult Liver | 2100 (n = 1) | 1390 ± 890 (n = 3) | 360 ± 270 (n = 3) | 32 (n = 1) |
| Embryo Liver | ND | 3190 (n = 1) | 620 (n = 1) | ND |

Naltrexone levels in ng/g tissue at different survival times;
dosage = 10 mg/kg delivered simultaneously Cumulative Injections of 6β-Naltrexol While 6β-naltrexol is relatively excluded from adult brain, it might accumulate slowly upon multiple dosing because of slow exit from the brain. Therefore, experiments were conducted to determine whether 6β-naltrexol accumulates in tissues over time after chronic delivery, and especially through retention in adult brain. After 4 injections of 6β-naltrexol over a 24 hr period (every 6 hrs), 6β-naltrexol levels were measured in fetal and maternal tissues 4 hrs after the last dose, and accumulation assessed in comparison to a single injection with a 4 hr survival. As shown in Table 2, a small increase of 6β-naltrexol occurred after cumulative injections with an average of ~1.5-fold for all tissues. However, this was not significant ($p>0.2$). Also, 6β-naltrexol trended towards greater accumulation in liver than brain ($p=0.084$ for comparison of adult liver vs adult brain after 4 injections). Likewise, 6β-naltrexol trended towards greater accumulation in embryos than adults ($p=0.063$ for compariopmentally equivalent to an early second trimester human (Clancy B, et al. (2001) Neurosci. 105:7-17; Workman A D, et al. (2013) J Neurosci. 33:7368-7383). This rodent-human developmental difference also extends to the BBB: in humans the BBB is widely thought to be nearly fully developed at or shortly after birth, while in mice, although controversial, it likely does not develop until PD14 or later (Lossinsky A S, et al (1986) Dev Neurosci 8:61-75; Ribatti D, et al. (2006) Anat Rec B New Anat. 289:3-8). If this is indeed the case then the early postnatal rodent could be a model to test BBB-dependent preventive effects of 6β-naltrexol on opioid dependence behaviors. Therefore the postnatal developmental time course of 6β-naltrexol's exclusion from the brain in mice was determined.

Figure 2A:
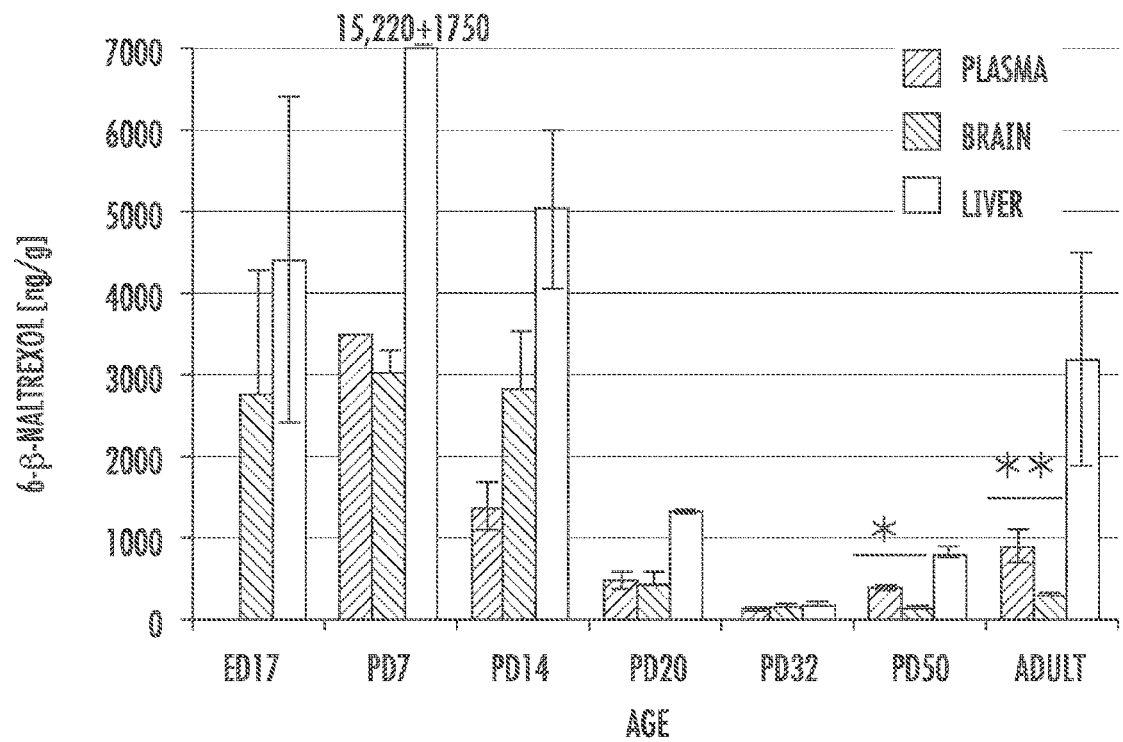
FIGS. 2A and 2B are bar graphs showing 6β-naltrexol levels (ng/g) in mice across tissue and development.
Figure 2B:
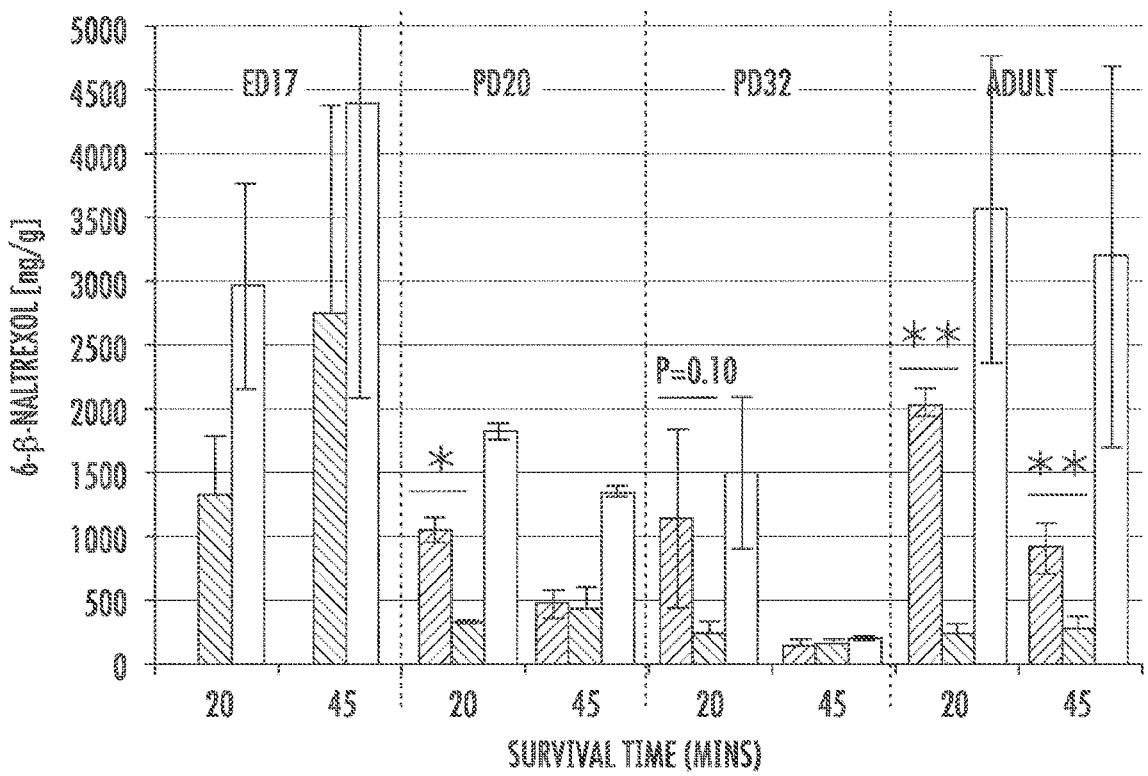
Figure 3A:
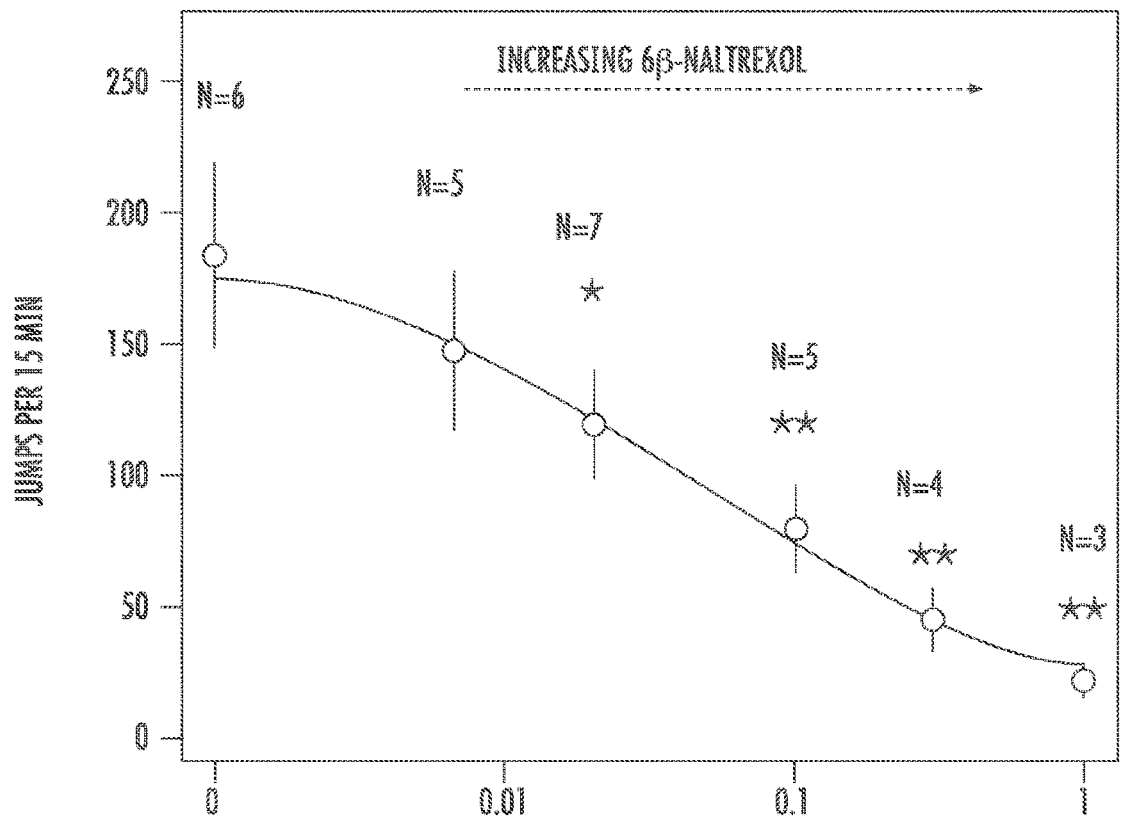
FIGS. 3A to 3C show 6β-naltrexol prevents opioid-induced withdrawal behavior in mice
Figure 3B:
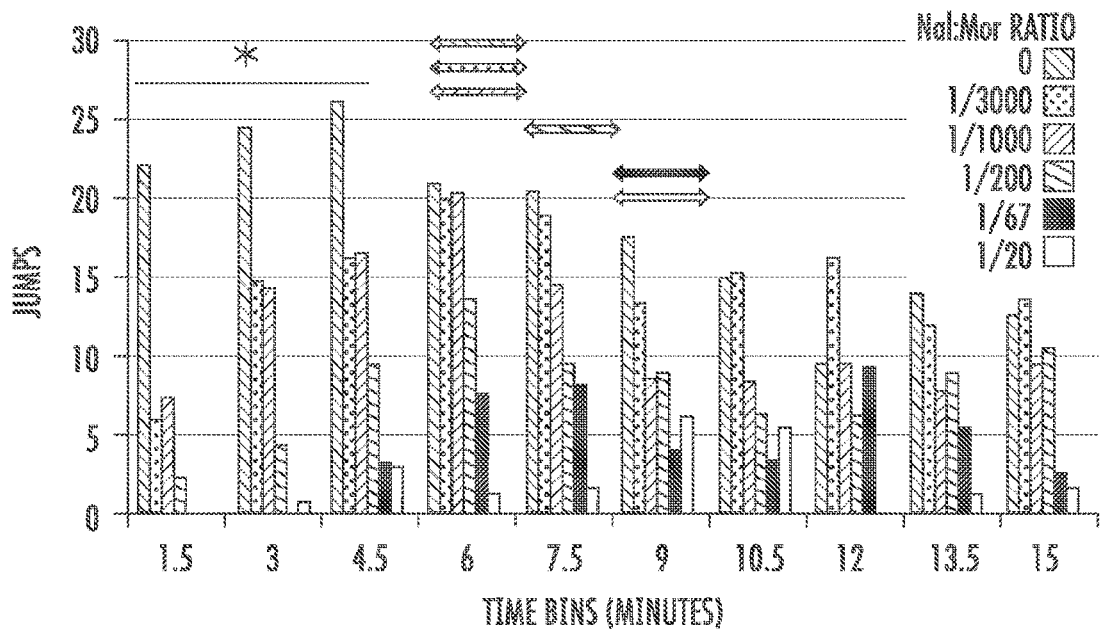
Figure 4:
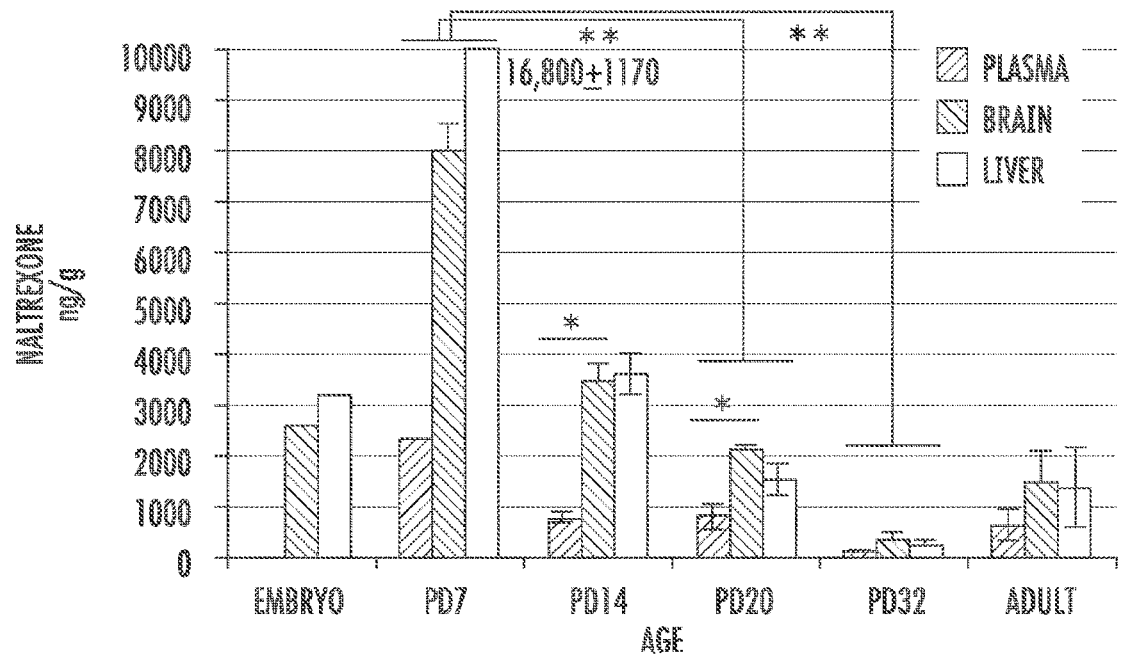
FIG. 4 is a bar graph showing naltrexone levels across tissues and development (45 minute survival time). Levels of drug in plasma, brain and liver after a single injection at PD7, PD14, PD20, and PD32. Embryonic (ED17) and adult (>2 mo old) data from Table 4 were added for comparison purposes. 45 min. survival time for all data. For the PD7 liver sample note that the data bar was truncated to better illustrate the broad range of drug levels across all tissues. Also note that the brain:plasma ratio is greater than unity in all cases; n=1 for embryonic brain and liver, PD7 plasma, and PD32 plasma, and n=2 or more for all other samples. Asterisks indicate either differences across age, or plasma vs brain differences at a particular age. *$p<0.05$; **$p<0.01$

A single injection of 6β-naltrexol was made in mice at PD7, PD14, PD20, PD32, and PD50, and drug levels measured after 45 minutes (data for embryos and adults were added for comparison). As shown in FIG. 2A, 6β-naltrexol levels in mice in plasma, brain, and liver varied over a wide range during postnatal development as a result of drastically changing clearance rates. Plasma levels decreased progressively from 3660+350 ng/ml at PD7 to 170+30 ng/ml at PD32, then reversed to 930+220 ng/ml in adults. Levels in the brain and liver roughly followed the same general pattern, with values in liver far exceeding those in all other tissues, especially during early postnatal development (PD7 and PD14). Most importantly, 6β-naltrexol levels in brain were stable from ED17 until PD14, but dropped precipitously by PD20, suggesting that the BBB develops in the time-frame from PD14-PD20. This interpretation is complicated, however, by dramatic changes in 6β-naltrexol clearance resulting in very low levels at PD20 and PD32 in all tissues. Clearly, at the 45 min survival time point, ratios between tissues cannot be accurately assessed if 6β-naltrexol has been nearly completely cleared from the system. However, surveying the data at 20 min post administration reveals that effective brain exclusion of 6β-naltrexol was evident at PD20 and PD32 (FIG. 2B). Table 3 summarizes the brain:plasma and liver:plasma KP ratios for the indicated survival time points, showing that levels are lower in brain than plasma at PD20 and older (with ratios that range from 0.22-0.35). In contrast the levels in liver are higher than in plasma at all ages (with KP ratios that range from 1.3-4.2). Thus, the exclusion of 6β-naltrexol from brain starting at PD20 is unique to that tissue. Also, the brain:plasma ratio for naltrexone is greater than unity at all ages (FIG. 4), consistent with its previously reported ability to cross the BBB (Kastin, A J, et al. (1991) Pharmacol Biochem Behav 40:771-774; Wang, D, et al. (2004) J Pharmacol Exp Ther 308:512-520). This is in stark contrast to the data for 6β-naltrexol.

of morphine), withdrawal jumping is 94% reduced. The lowest 6β-naltrexol dose tested, 0.0033-0.0066 mg/kg (=1/3000th that of morphine) caused a 20% decrease in jumping. There is also a time component to the effect of 6β-naltrexol on jumping behavior (FIG. 3B). As 6β-naltrexol levels were increased the jumps observed in a 15 minute testing bout were increasingly delayed. In addition, not shown in the figure, the latency-to-first-jump increases from 38+8 sec with no 6β-naltrexol to 128+44 sec at the lowest dose of 6β-naltrexol (1/3000th the dose of morphine) (p=0.05), to 118+31 sec at 0.01-0.02 mg/kg (1/1000th the dose of morphine) (p<0.05), to 163+46 sec at 0.05-0.1 mg/kg (1/200th the dose of morphine) (p<0.05), to 345-54 sec at 0.15-0.3 mg/kg (1/67th of the dose of morphine) (p<0.001). Therefore, even at extremely low doses, 6β-naltrexol reduces withdrawal jumping. Examining the first three time bins (up to 4.5 mins; see FIG. 3B) there were 73+28 total jumps with no 6β-naltrexol, trending lower to 37+29 jumps with 0.0033 mg/kg drug, again, not quite reaching significance (p=0.07). The drop in jumps reaches significance with the next highest doses of 6β-naltrexol. 0.01 and 0.05 mg/kg (p<0.05; asterisk in FIG. 3B).

Figure 3C:
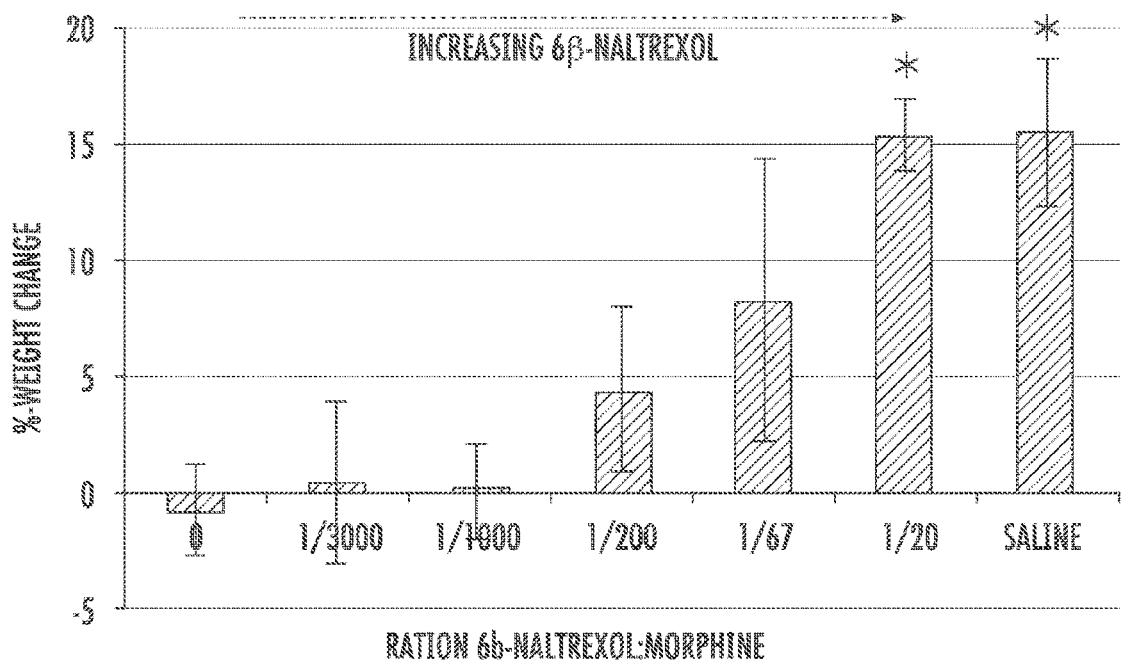

During the treatment period there was a significant inhibition of weight-gain as a result of morphine presentation alone, which is alleviated by increasing concomitant doses of 6β-naltrexol (FIG. 3C). Survival was 100% for all conditions and for all animals tested by this procedure. In mice with low weight gain because of morphine normal weight was usually restored by days 7-10 after treatment.

DISCUSSION

This example identifies a new paradigm for preventing NAS in neonates born to mothers engaged in opioid main-

TABLE 3

6β-naltrexol brain and liver $K_p$ ratios during postnatal development in mice

| Age | Survival time (min) | Plasma (ng/ml) | Brain (ng/g) | Liver (ng/g) | Brain: Plasma | Liver: Plasma |
|---|---|---|---|---|---|---|
| PD7  | 45 | 3513       | 3030 ± 340  | 15220 ± 1750 | 0.86 | 4.3 |
| PD14 | 45 | 1410 ± 370 | 2860 ± 800  | 5050 ± 1260* | 2    | 3.6 |
| PD20 | 20 | 1070 ± 100 | 350 ± 20*   | 1830 ± 70*   | 0.33 | 1.7 |
| PD32 | 20 | 1160 ± 730 | 260 ± 80    | 1510 ± 640   | 0.22 | 1.3 |
| PD50 | 45 | 430 ± 40   | 150 ± 10*   | 820 ± 80*    | 0.35 | 1.9 |

*p < 0.05 for comparison of brain or liver to plasma

Suppression of Dependence Behavior by 6β-Naltrexol

Considering that 6β-naltrexol continues to penetrate the brain at high levels prior to PD20 experiments were conducted to determine whether concomitant administration of 6β-naltrexol reduces withdrawal behaviors in pre-weaning age mice. A morphine dosing schedule was adapted based on studies in early postnatal rats and adult mice (Kest B. et al. (2002) Neuroscience 115:463-469; Jones, K L, et al. (1995) Behav. Neurosci. 109:1189-1198). Mice were injected with morphine alone, with morphine in combination with increasing concentrations of 6β-naltrexol, or saline alone, starting at P12 and continuing for 6 days. Withdrawal was then induced with an injection of naloxone. There was robust jumping characteristic of adult withdrawal behavior (Kest B, et al. (2002) Neuroscience 115.463-469), but not previously reported for pre-weaning mice or rats to our knowledge. Shown in FIG. 3A, this behavior is suppressed by increasing concentrations of 6β-naltrexol with an inhibitory dose 50 (ID50) of 0.022-0.044 mg/kg, which is 1/450th the morphine dose. At the highest dose tested, 0.5-1.0 mg/kg (=1/20th that tenance therapy. An opioid antagonist that is largely excluded from the maternal brain (enabling ongoing opioid therapy), but which is able to penetrate the placenta and immature BBB in the fetus, can protect the fetus from opioid exposure and thereby prevent NAS. Previous studies had already indicated that the opioid antagonist, 6β-naltrexol, is largely excluded from the brain while acting as a potent antagonist in the periphery (Wang, D, et al. (2004) J Pharmacol Exp Ther 308:512-520; Yancey-Wrona J E, et al. (2009) Life Sci. 85:413-420; Yancey-Wrona J, et al. (2011) Pain Med. 12:1727-1737), limiting peripheral adverse opioid effects such as constipation. Evidence is provided here that 6β-naltrexol readily enters the fetal circulation and fetal brain, resulting in substantially higher levels in fetal compared to maternal brain.

The ability of 6β-naltrexol to prevent opioid dependence in preweaning juvenile mice when the BBB is still immature was also examined. When administered in combination with morphine for several days during a period when the mouse BBB is still undeveloped, 6β-naltrexol prevents withdrawal behavior with extreme potency, owing to ready access to the neonatal brain lacking full BBB protection (ID50 0.022-0.044 mg/kg). This 6β-naltrexol dose is ~500-fold lower than the morphine dose used for inducing dependence, and is 20- to 500-fold lower than the ID50 of 6β-naltrexol for the blockade of opiate antinociception in adults depending on the agonist used and the route (and timing) of administration (Yancey-Wrona J E, et al. (2009) Life Sci. 85:413-420; Wang D, et al. (2001) J Neurochem. 77:1590-1600; Sirohi S, et al. (2009) J Pharmacol Exp Ther. 330:513-519). The extreme potency of 6β-naltrexol is further highlighted by the observation that even at a dosage that is 1/3000th that of morphine there is a 20% reduction in quantifiable withdrawal behavior. Efficacy of 6β-naltrexol is also quite high, with nearly complete suppression of juvenile withdrawal (94%) at the highest dose tested in the current example. Based on these results, 6β-naltrexol can be utilized in pregnant women undergoing opioid maintenance treatments to selectively block fetal dependence without interfering with the mother's pain and/or maintenance therapy.

Most of the existing treatment regimens for NAS rely on reducing the severity of symptoms, but are not preventive A 5-HT antagonist, ondansetron, recently entered clinical trials for prevention of NAS symptoms when delivered maternally shortly before birth and continuing in the postnatal period (Elkomy M H, et al. (2015) Clin Pharmacol Ther. 97:167-176). However, this treatment, while designed to reduce the length of stay in the ICU, would not be expected to prevent the occurrence of dependence and any related developmental consequences. These results indicate that prenatal therapy of the mother with 6β-naltrexol could be combined with other palliative therapies to reduce NAS substantially. Any reduction in fetal opioid dependence during pregnancy could yield considerable benefit in fetal development, term-delivery, weight gain, and short- and long-term sequelae of NAS.

The current example further reveals substantial changes in both 6β-naltrexol and naltrexone clearance across developmental age in mice. A similar profile across early human development has been reported for half-lives of a broad panel of 45 drugs, including glucuronidated drugs such as morphine (Ginsberg G, et al. (2002) Toxicol Sci. 66:185-200). The studied drugs generally display a long half-life in premature and full-term neonates, then the half-life decreases progressively over several months after birth, even below adult values, and then recovers to adult levels. This time course was attributed at least partly to the immaturity of hepatic and renal systems in the early postnatal period. The disclosed example shows a surprising stability of 6β-naltrexol from embryogenesis through the first two weeks after birth, after which levels drop precipitously as a result of increased clearance. This indicates that in addition to the known developmental delay in the brain of mice compared to humans at birth, there may also be a delay in developmental processes affecting drug metabolism and renal clearance in the postnatal period (6β-naltrexol is cleared both renally and by metabolism).

In conclusion, the combined properties of 6β-naltrexol, 1) a neutral antagonist of the μ-opioid receptor with low propensity to cause withdrawal compared to naloxone and naltrexone, 2) its relative exclusion from the adult CNS, and 3) its ability to enter the fetal circulation and brain show its utility and importance for preventive therapy for NAS. In addition to its potency and efficacy, 6β-naltrexol is the main metabolite of naltrexone in humans (but not in mice), which is FDA approved for the treatment of alcoholism (Pettinati, H. M, et al. (2006) Journal of clinical psychopharmacology 26:610-625) Therefore, 6β-naltrexol's known safety profile can facilitate its use in pregnant women.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating or preventing neonatal withdrawal or abstinence syndrome, comprising:
   prenatally administering to a drug dependent or opioid tolerant pregnant subject receiving opioid therapy or maintenance a first composition comprising an opioid antagonist in an amount effective to reduce or prevent the neonatal withdrawal or abstinence syndrome, wherein the opioid antagonist is a neutral antagonist to a μ-opioid receptor; and
   postnatally administering to a drug dependent or opioid tolerant infant subject a second composition comprising the opioid neutral antagonist in increasing amounts effective to facilitate weaning the infant from continued opioid maintenance administered when neonatal abstinence is observed.

2. The method of claim 1, wherein the opioid antagonist comprises 6β-naltrexol.

3. The method of claim 1, wherein the opioid antagonist is delivered in two daily sub-doses.

4. The method of claim 1, wherein the opioid antagonist is delivered in a daily dosage range from about 0.1 mg to about 100 mg.

5. The method of claim 1, wherein the opioid antagonist is comprised in a sustained drug release formulation.

6. The method of claim 1, wherein the opioid antagonist is orally available.

7. The method of claim 1, further comprising administering a palliative therapy to the pregnant subject and/or the infant subject.

8. The method of claim 1, further comprising administering a 5-HT antagonist to the pregnant subject and/or the infant subject.

9. The method of claim 8, wherein the 5-HT antagonist is ondansetron.

10. The method of claim 1, wherein the opioid antagonist reaches fetal circulation in sufficient amounts to reduce or reverse fetal opioid dependence.

* * * * *